United States Patent [19]

Morris et al.

[11] Patent Number: 5,501,659
[45] Date of Patent: Mar. 26, 1996

[54] ANKLE BRACE

[75] Inventors: James C. Morris; Joe G. Stetman, both of Rancho Santa Fe, Calif.

[73] Assignee: Smith & Nephew DonJoy, Inc., Carlsbad, Calif.

[21] Appl. No.: 226,290

[22] Filed: Apr. 11, 1994

Related U.S. Application Data

[63] Continuation-in-part of Ser. No. 14,649, Feb. 8, 1993, abandoned.

[51] Int. Cl.$^6$ ........................................................ A61F 5/00
[52] U.S. Cl. ................................ 602/27; 602/23; 602/62; 602/65; 128/882; 2/22
[58] Field of Search ...................... 602/5, 27, 46, 602/65, 23, 26; 623/27, 47; 2/22; 128/882

[56] References Cited

U.S. PATENT DOCUMENTS

| | | |
|---|---|---|
| Re. 33,762 | 12/1991 | Lonardo . |
| 487,492 | 12/1892 | Pugsley . |
| 830,894 | 9/1906 | Garrod . |
| 1,465,233 | 8/1923 | Posner . |
| 2,694,395 | 11/1954 | Brown . |
| 2,774,152 | 12/1956 | Alber . |
| 2,830,585 | 4/1958 | Weiss . |
| 3,028,861 | 4/1962 | Shapiro . |
| 3,298,365 | 1/1967 | Lewis . |
| 3,674,023 | 7/1972 | Mann . |
| 4,013,070 | 3/1977 | Harroff . |
| 4,280,489 | 7/1981 | Johnson, Jr. . |
| 4,289,122 | 9/1981 | Mason et al. . |
| 4,323,058 | 4/1982 | Detty . |
| 4,414,965 | 11/1983 | Maudlin et al. .................. 602/27 X |
| 4,459,980 | 7/1984 | Perser et al. . |
| 4,489,719 | 12/1984 | Lapenskie .......................... 602/27 |
| 4,510,927 | 4/1985 | Peters . |
| 4,628,945 | 12/1986 | Johnson, Jr. . |
| 4,771,768 | 9/1988 | Crispin . |
| 4,844,094 | 7/1989 | Grim . |
| 4,955,149 | 9/1990 | Otheri ................................. 602/27 X |
| 4,966,134 | 10/1990 | Brewer . |
| 5,022,390 | 11/1991 | Whiteside . |
| 5,067,486 | 11/1991 | Hely . |
| 5,088,478 | 2/1992 | Grim ................................... 602/27 |
| 5,094,232 | 3/1992 | Harris et al. ...................... 602/27 X |
| 5,109,613 | 5/1992 | Van Dyke . |
| 5,125,400 | 6/1992 | Johnson, Jr. ...................... 602/13 |
| 5,176,623 | 1/1993 | Stetman et al. ................... 602/27 |
| 5,213,564 | 5/1993 | Johnson, Jr. et al. ............. 602/27 |
| 5,217,324 | 6/1993 | Hall . |
| 5,368,551 | 11/1994 | Zuckerman ...................... 607/27 X |

OTHER PUBLICATIONS

*Orthotics and Prosethetics*, Sep. 1970, "Brace–to–Body Dynamics", pp. 21–29.
*Atlas of Orthotics*, The C. V. Mosby Co., 1985, "Lower Limb Orthoses", pp. 199–209, 227, 236; Functional Fracture Bracing, pp. 358–362, 370; Orthoses for Athletic Injuries, pp. 407–408.
*Foot Orthoses*, Williams & Wilkins, 1990, "Ankle–Foot Orthoses", pp. 125–135.
Catalog of Professional Care Products, Incorporated.

*Primary Examiner*—Richard J. Apley
*Assistant Examiner*—Kim M. Lee
*Attorney, Agent, or Firm*—Juettner Pyle Lloyd & Piontek

[57] ABSTRACT

An ankle brace to be fitted about the lower leg and ankle of a wearer for inhibiting inversion and eversion of the ankle while accommodating plantar flexion and dorsiflexion is characterized by a rigidifying and unitizing external shell comprising a unitary member made of a rigid material and including a leg encircling portion at least substantially encircling the lower leg of the wearer and ankle stays extending downwardly from the leg encircling portion over the ankle and down to the heel on both the medial and lateral sides of the leg, the leg encircling portion accommodating flexing of the sides of the shell about a vertical axis intermediate the ankle stays for movement of the sides and the stays horizontally into supporting engagement with the medial and lateral sides of the leg and ankle, the shell preventing undesired movement of the ankle stays relative to one another. The ankle brace also features a metatarsal support extending from the region of the metatarsals over the lateral side and instep of the wearer's foot to the medial side of the shell, where the shell provides a rigid post for anchoring the metatarsal support.

19 Claims, 2 Drawing Sheets

ANKLE BRACE

CROSS REFERENCE

This application is a continuation-in-part of application Ser. No. 08/014,649, filed Feb. 8, 1993, abandoned.

FIELD OF THE INVENTION

This present invention relates to ankle braces for inhibiting inversion and eversion of the ankle while permitting freedom of movement for plantar flexion and dorsiflexion.

BACKGROUND

Ankle braces for inhibiting inversion and eversion of the ankle while permitting relatively uninhibited plantar flexion and dorsiflexion of the foot, or for controlling plantar flexion and/or dorsiflexion, have been available for many years, indeed since at least the turn of the century.

With the advent of modern materials of construction, especially plastics, the braces have become lighter, less cumbersome, more easily fitted to and removed from the leg and ankle, and better adapted to the performance of their intended functions.

Of late, one ankle brace that has acquired particular acceptance is the so-called stirrup ankle brace, representative examples of which are illustrated in the patent to Glenn W. Johnson, Jr. U.S. Pat. No. 4,280,489 and the patent to Tracy Grim U.S. Pat. No. 4,844,094. As shown by these patents, the brace comprises a base member on which the heel of the wearer rests, a pair of rigid side members hingedly connected to opposite sides of the base member and extending upwardly on opposite sides of the ankle and along the lower leg, a pair of cushioning pads respectively coextensive with and secured to the inner surfaces of the side members for cushioning the leg and ankle, and a pair of leg encircling straps adapted to be wrapped about the lower leg and the two side members to hold the side members in place with the pads firmly and snugly engaging the opposite sides of the leg and ankle.

When applied to the leg and ankle, the side members inhibit inversion and eversion, i.e., twisting, of the ankle, but the brace is open to the front and rear and thereby permits normal plantar flexion and dorsiflexion. The brace is designed to be received in a conventional shoe, whereby the wearer may engage in normal activities, such as walking, running and sports activities, while the ankle is protected against inversion and eversion. The Grim patent also provides a counter strap at the achilles tendon and eyelets on the front edges of the side members so that the brace can be tied to the wearer's shoe by the lace of the shoe, thereby to gain further support.

While the stirrup ankle brace is an effective product which has gained wide acceptance, it does suffer a problem referred to as "pistoning". Specifically, because the side members are of necessity hingedly connected to the base member (so that the side members can be swung into engagement with the leg and ankle), the two side members tend to reciprocate vertically up and down in an alternating relationship to one another, much like the pistons of an internal combustion engine, thus the term "pistoning". This is, of course, a source of irritation to the wearer and detracts from the effectiveness of the brace.

Also, problems are frequently encountered in fitting the side members to the leg. Inasmuch as the two side members are independently movable, and the two leg encircling straps are the only means provided for locating each side member relative to the leg and for holding the side members in place relative to one another and the leg, it is necessary for each of the straps to be secured to both of the side members and for at least one of the points of securement to be adjustable. This is customarily accomplished by forming the straps from a fabric having a plush surface and by securing patches of fabric hook material (such as the well known product sold under the trademark "VELCRO" and equivalents thereof) to the exterior surfaces of both of the side members for releasable locking engagement with the plush surfaces of the strap. Due to the necessity for locking both of the side members to the straps, the tension on a given strap around the circumference of the leg is rarely uniform, i.e., the tension on the portion of the strap passing between the side members posteriorly of the leg is frequently different from the tension on the portion of the strap passing between the side members anteriorly of the leg. Also, the tension on the two straps is frequently different. This in turn can result in a poor fit, further detracting from the effectiveness of the brace.

SUMMARY OF THE INVENTION

It is an object of the invention to provide an ankle brace having all of the advantages and none of the disadvantages of the stirrup ankle brace.

It is a further object of the invention to provide an ankle brace having significant additional advantages not within the purview of and incapable of attainment by the stirrup ankle brace.

A primary feature of the invention resides in the provision of an ankle brace characterized by an integral essentially rigid shell that unitizes and completely rigidities the brace, instead of having a stirrup comprised of three individual and independently movable members.

In accordance with the invention, the integral shell is formed of a substantially rigid material, preferably a moldable plastic, and comprises a leg encircling portion adapted to at least substantially encircle the lower leg of the wearer and a pair of ankle stays extending downwardly from the leg encircling portion over the ankle and down to the heel of the wearer on both the medial and lateral sides of the leg. The leg encircling portion accommodates flexing of the sides of the shell about a vertical axis intermediate the ankle stays for accommodating movement of the sides of the shell and the ankle stays horizontally into firm supporting engagement with the medial and lateral sides of the wearer's leg and ankle. Because of its integral construction and substantial rigidity, the shell unitizes the ankle stays with one another and prevents vertical movement of the same relative to one another, thereby eliminating the objectionable "pistoning" problem of stirrup ankle braces.

Additionally, since the ankle stays are unitized and not independently movable, it is not normally necessary to secure or anchor the leg encircling attachment straps to both sides of the brace or to both of the ankle stays. The straps need be secured only to one side of the shell or one stay without further attachment to the shell, whereby the straps exert a uniform pressure around the entire circumference of the leg. The unitized shell and the mounting of the securing straps as provided in accordance with the invention thereby eliminate the fitting problem encountered with stirrup ankle braces.

Another feature of the invention resides in the provision of a unitary cushioning boot to be applied to the lower leg, ankle and foot of the wearer, in lieu of the pair of independent, limited area cushioning pads employed in stirrup ankle braces. The unitary boot provides a better and more comfortable fit of the brace to the leg, ankle and foot of the wearer and contributes to elimination of the fitting problem incurred with stirrup ankle braces. Also, by securing the shell to the boot, suitably by releasable fabric hook and plush connections, the boot also contributes to the unitization of the brace construction, especially unitization of the ankle stays.

A third important feature of the invention resides in the recognition that twisting of the ankle, especially eversion of the ankle, customarily commences in the region of the fifth metatarsal of the foot, i.e., adjacent the little toe, and the realization that the shell of the present invention in essence comprises a rigid post for gaining a hindfoot lock on the fifth metatarsal. In accordance with the invention, metatarsal support, and therefore further stabilization of the ankle, is achieved by extending a strap from the region of the fifth metatarsal upwardly over the lateral side and the instep of the foot to the medial side of the shell, where it is attached to and anchored by the shell. This results in substantially improved stabilization for the ankle. While flexion of the foot, especially plantar flexion may be inhibited to a degree, the enhanced stabilization is of greater significance, especially during rehabilitation of an ankle injury.

The foot encircling portion of the cushioning boot of the invention provides for convenient attachment of the metatarsal support and also contributes to the stabilizing influence of the support.

Thus, the present invention provides significant advantages over prior ankle braces, especially stirrup ankle braces.

These and other advantages and objects of the invention will become apparent from the following detailed description, as considered in conjunction with the accompanying drawings.

DETAILED DESCRIPTION

The following is a detailed description of an embodiment of the ankle brace of the invention which is presently deemed by the inventors to be the best mode of carrying out their invention.

Figure 1:
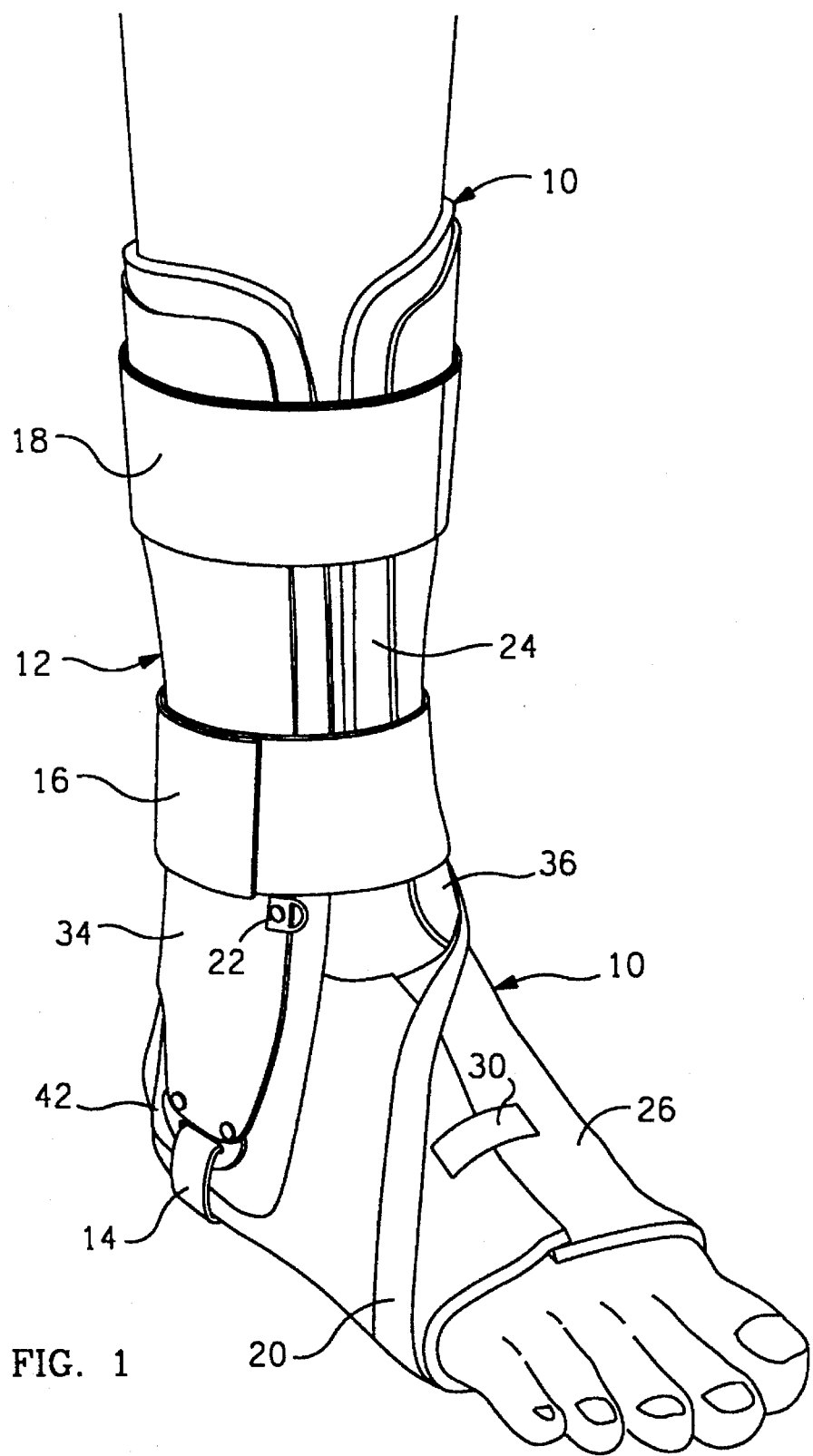
FIG. 1 is a frontal perspective view of a preferred embodiment of the ankle brace of the invention as adapted for and applied to the right foot of a wearer.
Figure 2:
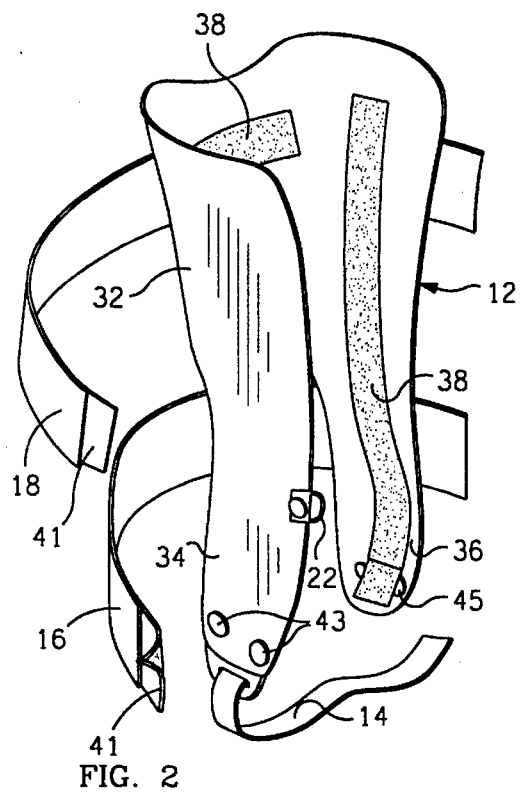
FIG. 2 is a frontal perspective view of a preferred embodiment of a shell that comprises one element of the preferred embodiment of the ankle brace illustrated in FIG. 1.
Figure 3:
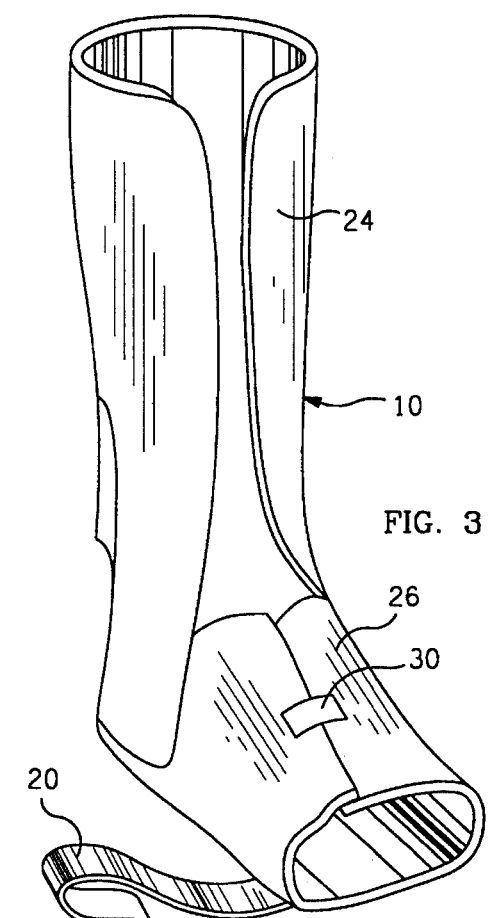
FIG. 3 is a frontal perspective view of a preferred embodiment of a cushioning boot that comprises another element of the preferred embodiment of the ankle brace illustrated in FIG. 1.
Figure 4:
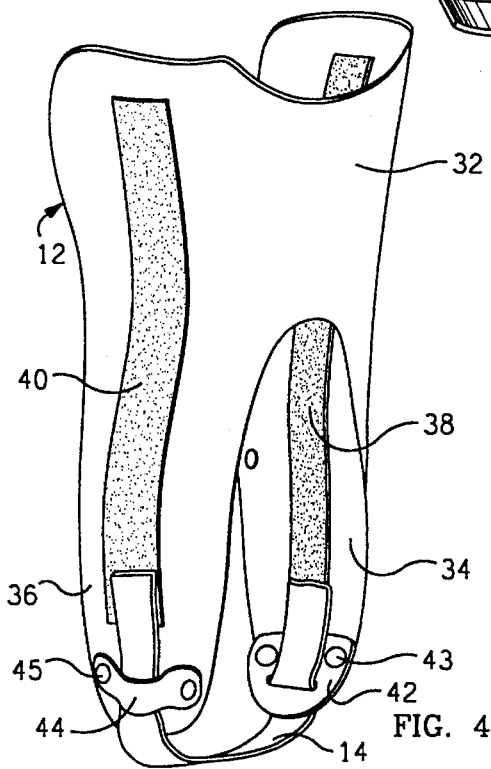
FIG. 4 is a perspective view showing the back of the shell illustrated in FIG. 2.
Figure 5:
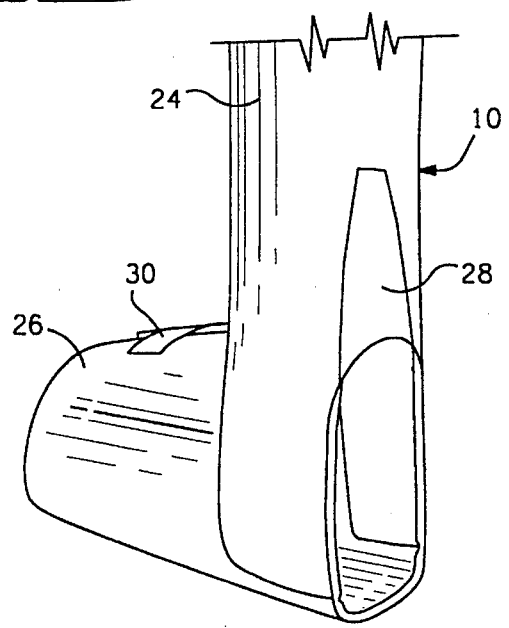
FIG. 5 is a perspective view showing the back of the cushioning boot illustrated in FIG. 3.

Referring to the drawings, the ankle brace of the invention is comprised of a unitary cushioning boot 10 (FIGS. 3 and 5), an integral and substantially rigid outer shell 12 (FIGS. 2 and 4), a flexible heel strap 14, a pair of flexible leg encircling straps 16 and 18, and a flexible metatarsal support strap 20. Eyelets may optionally be provided at the front edges of the shell 12 for reception of the shoelaces of the wearer's shoe when a shoe is worn over the brace. However, it is preferred in practice of the present invention to use only one eyelet, specifically an eyelet 22 at the front edge on the lateral side of the brace.

The boot 10 is preferably made of single ply fabric covered neoprene conformable to the leg, ankle and foot of the wearer and having a plush exterior surface for reception of Velcro or equivalent fabric hook attachment means provided within the interior of the shell 12 and on the metatarsal strap 20. The boot is comprised of a leg encircling portion 24 and a foot encircling portion 26. The leg encircling portion, including the parts thereof that cover the malleoli of the wearer's ankle, are preferably formed of a relatively thick neoprene sheet providing a cushion for the leg and malleoli, while the foot and heel encircling portion is preferably formed of a thinner neoprene to accommodate reception of the brace within the shoe of the wearer. The heel is preferably left open at the rear and that part 28 of the leg encircling portion 24 just above the heel is preferably formed of the thinner neoprene material so that the portion of the boot covering the wearer's achilles tendon is somewhat resilient or yieldable. All three of the components 24, 26 and 28 of the boot are securely stitched together to form a unitary assembly.

The foot encircling portion 26 is slit or open at the top so that the same can be wrapped about the wearer's foot, overlapped over the instep of the foot, and secured in place by a small strap 30 of Velcro or a like fabric hook material. The leg encircling portion 24 may be formed in the same overlapping fashion or may simply be open at the front as illustrated. Forms of construction other than as illustrated and described may of course be used within the knowledge in the art to fabricate boots comparable to the boot 10.

The shell 12 is an integral, substantially rigid element comprised of a leg encircling portion 32 and depending and stays 34 and 36 which extend downwardly to the heel and overlie the ankle on both sides of the wearer's leg and foot. In the preferred embodiment, the leg encircling portion 32 includes opposed sides and a curved back or posterior wall integrally connecting the sides. However, the curved connecting wall can, when desired, extend around the anterior or front side of the leg. Specifically, the fight leg shell 12 illustrated in the drawings can be reversed and applied to the left leg with the connecting portion at the front or anteriorly of the leg, without loss or diminution of the advantages of the shell. As an alternative, the leg encircling portion could completely encircle the leg by providing overlapping end portions on the side of the shell opposite the connecting wall. As is customary, and as illustrated, the ankle stays 34 and 36 are molded or configured to accommodate the malleoli on the respective sides of the ankle.

The material from which the shell is made, preferably a molded plastic, is essentially rigid vertically, horizontally and transversely. However, due to the configuration of the shell, the sides of the shell can be flexed horizontally toward one another about a vertical axis intermediate the ankle stays, i.e., in the illustrated embodiment, a vertical axis substantially coincident with the center line of the connecting wall of the shell, so that the shell and the ankle stays can be conformed to the boot 10 and the leg and ankle of the wearer.

Preferably, strips 38 of Velcro or a like hook material are provided on the interior of the shell so that, once the boot and shell have been fitted to the leg and ankle, the boot will remain associated with the shell and the brace may be removed from and reapplied to the leg and ankle without need for refitting.

Once fitted about the leg and ankle, the boot and shell may be secured to the leg by wrapping the leg encircling straps 16 and 18 about the shell, with one strap 16 just above the ankle and eyelet 22 and the other strap 18 near the top of the shell. The straps are formed of fabric having plush, i.e., hook receptive surfaces. A vertical strip 40 of Velcro or the like of nearly the same height as the shell is secured to the exterior surface of one side of the shell, preferably the medial side, so that one end of each of the straps 16 and 18 can be secured to the shell to facilitate wrapping of the straps about the shell and the lower leg. The other end of each strap has a tip 41 of Velcro or a like hook material for securing the strap upon itself after it has been wrapped around the leg and shell.

Velcro hook material need not be provided on the exterior of the other, i.e., lateral, side of the shell, because it is not needed to locate or position the lateral stay. Consequently, each of the straps 16 and 18 will slip relative to the lateral side of the shell and thereby exert a uniform pressure around the entire circumference of the shell, the ankle stays and the wearer's leg. However, if necessary to prevent migration, a patch of hook material can be applied to the lateral stay, especially for the lower strap 16. The upper strap 18 is preferably resilient to avoid excessive pressure on the shin and to prevent the strap from digging into the boot 10.

The heel strap 14, which is formed of a plush surfaced fabric, has one end threaded through a slot in a flexible fitting 42 at the bottom of the lateral ankle stay 34 and is secured to the Velcro hook material 38 on the interior surface of the lateral stay. The other end of the heel strap 14 is adapted to be threaded through a loop 44 on the exterior surface of the medial ankle stay 36 and to be adjustably secured to the Velcro strap 40 on the exterior of the medial sidewall of the shell in order to provide a final fitting of the shell to the heel of the wearer.

The fitting 42 on the lower end of the lateral stay 34 is formed of a soft and pliable plastic material, and serves as a shock absorber for the lower end of the lateral stay. The fitting is secured to the stay in any suitable manner, e.g., by means of rivets 43. The loop 44 is suitably formed of the same plastic and is similarly secured to the medial stay, e.g., by rivets 45.

Because of its integral construction and substantial rigidity, the shell 12 effectively unitizes and rigidifies the assembly and prevents vertical movement of the ankle stays 34 and 36 relative to one another. Consequently, the shell prevents occurrence of the "pistoning" problem encountered with stirrup-type ankle braces, i.e., alternating vertical reciprocation of the two sidewall members of the stirrup as the wearer walks or runs.

Also, because the shell maintains a fixed relationship between the ankle stays, the leg encircling straps 16 and 18 are not required to locate or position both of the stays relative to one another and to the wearer's leg. Consequently, the straps may be attached to only one stay (the medial stay) and simply slip relative to the other stay (the lateral stay) thereby to exert a uniform pressure on the shell, the stays and the leg, and thereby eliminate the fitting problems encountered with stirrup-type braces.

Additionally, it has been discovered that if the brace of the invention is to be tied to the wearer's shoe, it is preferably and far more advantageous to use a single eyelet 22 on just one of the ankle stays 34–36, preferably the lateral stay 34. This is in marked contrast to the stirrup ankle brace where, because the side members are individually movable, the shoe has to be tied to both side members.

The integral unitary shell 12 of the invention, especially as used in combination with the unitary boot 10, therefore constitutes a significant improvement in ankle braces, providing greater stability and support for an injured ankle or an ankle prone to injury by inversion or eversion.

The integral construction and substantial rigidity of the shell 12 also leads to further improvements in ankle brace design and construction for stabilizing and immobilizing an ankle, especially in terms of immobilizing the ankle against eversion.

Eversion of the ankle usually commences at a pivot point in the region of the fifth metatarsal of the foot (adjacent the little toe), with the foot rolling over on its outer edge inwardly under the ankle and the ankle shifting outward relative to the foot. Prior art ankle braces have been concerned with support of the ankle and have not addressed the problem of the foot turning or rolling inward under the ankle, other than to attempt to support the ankle rearwardly, and thus remotely, from the pivot point where eversion commences. Heretofore, there has been no rigid anchor capable of mitigating roll of the foot commencing in the region of the fifth metatarsal.

The ankle brace of the invention provides means for mitigating such roll. Specifically, a metatarsal support strap 20 extends from a point at the bottom of the foot in the region of the fifth metatarsal upwardly over the lateral side and the instep of the foot portion 26 of the boot 10, and is then wrapped around the me, dial side of the shell 12 which provides a hindfoot locking post and rigid anchor for the strap 20, whereby the strap 20 supports the foot directly in the region of the fifth metatarsal and prevents, or at least effectively minimizes, the tendency of the foot to roll relative to the shell and thus relative to the ankle.

To enhance the integrated or unitized construction of the brace, the foot encircling portion 26 of the boot 10 extends forwardly to the region of the metatarsals of the foot and the metatarsal strap 20 is attached to the sole of the boot in the region of the metatarsals, or at least the region of the fifth metatarsal.

The strap 20 preferably comprises a strip of Velcro or equivalent fabric hook material attached at one end of the sole of the boot, either by fixed stitching or by the detachable locking engagement of the hook material with the plush surface of the boot. The strap 20 also has detachable locking engagement with the exterior of the foot portion of the boot over the lateral side and instep of the boot. The strap is of a length to at least partially encircle the shell 12 and is anchored to the shell by detachable locking engagement with the plush surface of the strap 16, and/or the strap 18. The strap 20 thus supports the foot in the region of the metatarsals, and thereby provides for significantly improved stabilization of the ankle.

The strap 20, although often quite advantageous, is not strictly essential to the successful performance of ankle brace 10. The strap 20 may be marketed as an optional accessory for the ankle brace of the invention. In this event, it is necessary that strap 20 have detachable locking engagement with the exterior of boot 26, rather than fixed stitching.

The objects and advantages of the invention have therefore been shown to be attained in a practical, economical and facile manner.

While the drawings illustrate an ankle brace for the right leg, the brace of the invention is of course equally applicable to the left leg. The manner of making a brace for the left ankle will be obvious to the artisan from the accompanying drawings and the foregoing description.

The rigid shell 12 of the invention is also adapted for use by itself and/or with other ankle braces. For example, U.S. Pat. No. 5,067,486 discloses an ankle brace comprised of a laced-up boot with a plurality of ankle stabilizing straps that are secured at one end to the center of the posterior surface of the boot above the malleoli. By providing a vertical strap receiving slot in the portion of the shell extending to the rear of the leg, or by mounting the shell with the connecting portion at the front of the leg, the shell can be applied over the boot and then secured in place on the ankle by the stabilizing straps that are associated with the boot, thereby to provide a very stable support for an acutely injured ankle.

It will also be apparent that the rigid shell 12 may be utilized independently of an underlying boot or brace, and that the shell may be secured to the wearer's leg and ankle by means other than or in addition to straps, e.g., by conventional adhesive tape or by conventional elastic or inelastic bandages, such as those available under the trademark ACE and equivalents thereof.

As one example, the shell 12 may be secured directly to a wearer's leg and ankle by the straps 14, 16 and 18 without using the boot 10. In such event, the wearer would use a heavy weight fabric sock, e.g., an athletic sock, in lieu of the boot 10 in order to provide a cushion between the rigid shell and the wearer's leg and ankle. Alternatively, a layer of suitable cushioning material could be employed, especially between the ankle stays and the malleoli of the wearer's ankle.

In another example, the shell 12 alone, i.e., without the straps 14, 16 and 18, without the hook and pile fabrics, and without the fitting 42, loop 44 and eyelet 22, could be fitted to the leg and ankle and secured in place by an elastic bandage, inelastic bandages or straps, and/or conventional adhesive tape applied in a manner customarily employed for taping ankles, e.g., in the conventional FIG. 8 pattern. Again, it is advisable to use cushioning between the shell and the wearer's leg and ankle, particularly the ankle.

In the latter regard, it would be appropriate to affix cushioning material to the interior surface, or selected areas of the interior surface, of the shell 12. Suitable materials include neoprene, memory foam, gel pads, air bags and combinations of the same. These may either be adhered to the interior surfaces of the shell or detachably affixed to the shell by conventional hook and pile materials, e.g., VELCRO hook and pile materials. In one such example, the shell may be lined with fabric covered neoprene, and pads of memory foam may be attached thereto in those areas of the stays that overlie the malleoli.

Thus, while a preferred embodiment of the invention has been herein illustrated and described in detail, it is to be appreciated that various changes, rearrangements and modifications may be made therein without departing from the scope of the invention, as defined by the appended claims.

What is claimed is:

1. In a stirrup style ankle brace adapted to be inserted into a shoe and to be fitted about the lower leg and ankle of a wearer for inhibiting inversion and eversion of the ankle while accommodating plantar flexion and dorsiflexion of the foot, the improvement comprising:

a rigidifying shell having upper and lower ends, said shell consisting of a unitary member made of a substantially rigid material and including at its upper end a leg encircling portion adapted to at least substantially encircle a portion of the lower leg of the wearer above the wearer's ankle and achilles tendon and a pair of spaced apart ankle stays extending substantially vertically downward from opposite sides of said leg encircling portion over the ankle and down to the heel of the wearer on both the medial and lateral sides of the leg, said leg encircling portion accommodating flexing the sides of said portion about a vertical axis intermediate said ankle stays for accommodating movement of the sides of said portion and said ankle stays horizontally into firm supporting engagement with the medial and lateral sides of the wearer's leg and ankle, said shell having no contact with the posterior surface of the heel of the wearer and accommodating insertion of the lower ends of said ankle stays into the wearer's shoe, said unitary shell mitigating vertical movement of said ankle stays relative to one another.

2. In an ankle brace as set forth in claim 1, said leg encircling portion extending around the back and at least both sides of the wearer's leg.

3. In an ankle brace as set forth in claim 1, said leg encircling portion extending around the front and at least both sides of the wearer's leg.

4. In an ankle brace as set forth in claim 1, a metatarsal support extending from the region of the fifth metatarsal over the lateral side and instep of the wearer's foot to said shell, said unitary shell comprising a rigid post for anchoring said metatarsal support to said shell.

5. In an ankle brace as set forth in claim 1, cushioning means between at least the wearer's ankle and said ankle stays, and fastening means for flexing said shell into and for holding said shell and said cushioning means in firm engagement with the leg and ankle of the wearer.

6. In an ankle brace as set forth in claim 1, cushioning means on the interior surfaces of said shell at least in the areas of said ankle stays.

7. In an ankle brace as set forth in claim 6, said cushioning means comprises one or more of fabric, foam, gel pad and air bag.

8. In an ankle brace as set forth in claim 1, fastening means for holding said shell in firm engagement with the leg and ankle of the wearer, said fastening means comprising one or more of adhesive tape, elastic or inelastic bandage and straps.

9. In an ankle brace as set forth in claim 1, fastening means encircling said shell for holding said shell in firm supporting engagement with the leg and ankle of the wearer, said fastening means having means of attachment to a single location on said shell and encircling said shell without further attachment to said shell whereby said fastening means exerts a uniform pressure around the circumference of the wearer's leg.

10. In an ankle brace as set forth in claim 1 for insertion of the lower ends of said ankle stays into a shoe with laces, said shell including fastening means on one of said stays to receive a lace of the shoe.

11. In an ankle brace as set forth in claim 1, a heel strap extending between the lower ends of said ankle stays and adapted to extend under the wearer's heel, said heel strap having an adjustable connection with at least one of said ankle stays for fitting said stays to the heel of the wearer.

12. An ankle brace adapted to be fitted about the lower leg and ankle of a wearer for inhibiting inversion and eversion of the ankle while accommodating plantar flexion and dorsiflexion of the wearer's foot, comprising:

a unitary boot made of a flexible, conformable, cushioning material and including a leg encircling portion for encircling the lower leg of the wearer, ankle portions extending downwardly over the ankle on both the medial and lateral sides of the leg, and a foot portion extending under the heel of the wearer and secured to and interconnecting the lower ends of said ankle portions;

a rigidifying shell overlying said boot, said shell having upper and lower ends and comprising an integral member made of a substantially rigid material, said member including a leg encircling portion at its upper end adapted to at least substantially encircle a portion of the lower leg of the wearer above the ankle and achilles tendon and a pair of spaced apart ankle stays extending substantially vertically downward from opposite sides of said leg encircling portion over the ankle and down to the heel of the wearer on both the medial and lateral sides of the leg, said leg encircling portion of said shell accommodating flexing of the sides of said portion about a vertical axis intermediate said ankle stays for accommodating movement of the sides of said portion and said ankle stays horizontally into firm supporting engagement with the underlying portion of said boot and the medial and lateral sides of the wearer's leg and ankle; and fastening means for holding said shell in firm supporting engagement with the leg and ankle of the wearer, said shell having no contact with the posterior surface of the heel of the wearer and accommodating insertion of the boot and the lower ends of said ankle stays into the wearer's shoe.

13. An ankle brace as set forth in claim 12, wherein said leg encircling portion of said shell extends around the back and at least both sides of the wearer's leg.

14. An ankle brace as set forth in claim 12, wherein said leg encircling portion of said shell extends around the front and at least both sides of the wearer's leg.

15. An ankle brace as set forth in claim 12, wherein said fastening means comprises at least one of adhesive tape, elastic or inelastic bandage and shell encircling straps.

16. An ankle brace as set forth in claim 12, including a heel strap extending between the lower ends of said ankle stays and adapted to extend under the foot portion of said boot and the wearer's heel, said heel strap having an adjustable connection with at least one of said ankle stays for fitting said stays to the foot portion of said boot and the heel of the wearer.

17. An ankle brace as set forth in claim 12, including a metatarsal support extending from the region of the fifth metatarsal of the wearer's foot over the lateral side and instep of the foot to the medial side of said shell, said shell comprising a rigid post for anchoring said metatarsal support to said shell.

18. An ankle brace adapted to be fitted about the lower leg and ankle of a wearer for inhibiting inversion and eversion of the ankle while accommodating plantar flexion and dorsiflexion of the wearer's foot, comprising:

a unitary boot made of a flexible, conformable, cushioning material and including a leg encircling portion for encircling the lower leg of the wearer, ankle portions extending downwardly over the ankle on both the medial and lateral sides of the leg, and a foot portion extending under the heel and sole of the wearer's foot and secured to and interconnecting the lower ends of said ankle portions, said foot portion extending forwardly toward the region of the metatarsals of the wearer's foot;

a rigidifying shell overlying said boot, said shell having upper and lower ends and comprising a unitary member made of substantially rigid material, said member including a leg encircling portion at its upper end adapted to at least substantially encircle a portion of the lower leg of the wearer above the ankle and achilles tendon and a pair of spaced apart ankle stays extending substantially vertically downwardly from opposite sides of said leg encircling portion over the ankle and down to the heel of the wearer on both the medial and lateral sides of the leg;

said leg encircling portion of said shell accommodating flexing of the sides of said portion about a vertical axis intermediate said ankle stays for accommodating movement of the sides of said portion and said ankle stays horizontally into firm supporting engagement with the underlying portions of said boot and the medial and lateral sides of the wearer's leg and ankle;

said shell having no contact with the posterior surface of the heel of the wearer and accommodating insertion of the boot and the lower ends of said ankle stays into the wearer's shoe;

fastening means encircling said shell for holding said shell in firm supporting engagement with the leg and ankle of the wearer; and a metatarsal support attacked to said foot portion of said boot in the region of the metatarsals of the wearer's foot and extending upwardly over the lateral side and the instep of the foot to the medial side of said shell, said shell comprising a rigid post for anchoring said metatarsal support to said shell.

19. An ankle brace as set forth in claim 18, said foot portion of said boot and said fastening means having plush exterior surfaces for locking reception of fabric hook material and said metatarsal support comprising a strap including fabric hook material for lockingly engaging said foot portion and said fastening means.

* * * * *